United States Patent [19]

Ruoslahti et al.

[11] Patent Number: 5,169,930
[45] Date of Patent: Dec. 8, 1992

[54] FIBRONECTIN RECEPTOR

[75] Inventors: Erkki I. Ruoslahti, Rancho Sante Fe, Calif.; Guido Tarone, Turin, Italy; Filippo G. Giancotti, Del Mar; Bruce E. Vogel, San Diego, both of Calif.

[73] Assignee: La Jolla Cancer Research Foundation, La Jolla, Calif.

[21] Appl. No.: 461,349

[22] Filed: Jan. 5, 1990

[51] Int. Cl.$^5$ .......................... C07K 3/20; C07K 15/12
[52] U.S. Cl. ...................................... 530/350; 530/413
[58] Field of Search ........................ 530/350, 395, 413

[56] References Cited

PUBLICATIONS

Bodary et al., The Integrin Beta 1 Subunit Associates with the Vitronectin Receptor Alpha v Subunit to form a Novel Vitronectin Receptor in a Human Embryonic Kidney Cell Line, J. Biol. Chem. 265(11): 5938–5941 (1990) (Abstract only).

Dedhar et al., Isolation of a Novel Integrin Receptor Mediating Arg-Gly-Asp-Directed Cell Adhesion to Fibronectin and Type i Collagen from Human Neuroblastoma Cells Association of a Novel Beta-1-Related Subunit with Alpha-v, J. Cell. Biol., 110(6): 2185–2194 (1990) (Abstract only).

Joseph et al., Characterization of Chinese Hamster Ovary Cells with Impaired Spreading Properties on Fibronectin, J. Cell Sci (England) 96(PT 3): 519–526 (1990) (Abstract only).

Pierschbacher et al., Cell Attachment Activity of Fibronectin can be Duplicated by Small Synthetic Fragments of the Molecule, Nature 309: 30–33 (1984).

Cheresh et al., A Novel Vitronectin Receptor Integrin ($a_v B_x$) is Responsible for Distinct Adhesive Properties of Carcinoma Cells, Cell 57: 59–69 (1989).

Richard O. Hynes, Integrins: A Family of Cell Surface Receptors, Cell 48: 549–554 (1987).

John M. Gardner and Richard O. Hynes, Interaction of Fibronectin with its Receptor on Platelets, Cell 42: 439–448 (1985).

Erkki Ruoslahti and Michael D. Pierschbacher, New Perspectives in Cell Adhesion: RGD and Integrins, Science 238: 491–497 (1987).

Wayner et al., Identification and Characterization of the T Lymphocyte Adhesion Receptor for an Alternative Cell Attachment Domain (CS-1) in Plasma Fibronectin, The Journal of Cell Biology 109: 1321–1330 (1989).

Randall H. Kramer and Nancy Marks, Identification of Integrin Collagen Receptors on Human Melanoma Cells*, The Journal of Biological Chemistry 264: 4684–4688 (1989).

Pytela et al., Platelet Membrane Glycoprotein IIb/IIIa: Member of a Family of Arg-Gly-Asp-Specific Adhesion Receptors, Science 231: 1559–1561 (1986).

Ginsberg et al., Cytoadhesins, Integrins, and Platelets, Thrombosis and Haemostasis 59: 1–6 (1988).

Freed et al., A Novel Integrin B Subunit is Associated with the Vitronectin Receptor a Subunit ($a_v$) in a Human Osteosarcoma Cell Line and is a Substrate for Protein Kinase C, The EMBO Journal 8: 2955–2965 (1989).

Clayton A. Buck and Alan F. Horwitz, Cell Surface Receptors for Extracellular Matrix Molecules, Ann. Rev. Cell Biol. 3: 179–205 (1987).

Gehlsen et al., The Human Laminin Receptor is a Member of the Integrin Family of Cell Adhesion Receptors, Science 241: 1228–1229 (1988).

*Primary Examiner*—Jeffrey E. Russel
*Attorney, Agent, or Firm*—Campbell and Flores

[57] ABSTRACT

The present invention provides a substantially pure integrin-type receptor characterized in that it consists of an $a_v$ and a $\beta_1$ subunit. The $a_v\beta_1$ integrin binds to fibronectin and GRGDSPK but does not bind to vitronectin. The $a_v\beta_1$ integrin can be used to determine the presence of a $a_v\beta_1$ ligand and to develop adhesion peptides specific for the various integrins. The presence of the $a_v\beta_1$ integrin can be used to assess ability of cells to adhere to fibronectin.

1 Claim, 2 Drawing Sheets

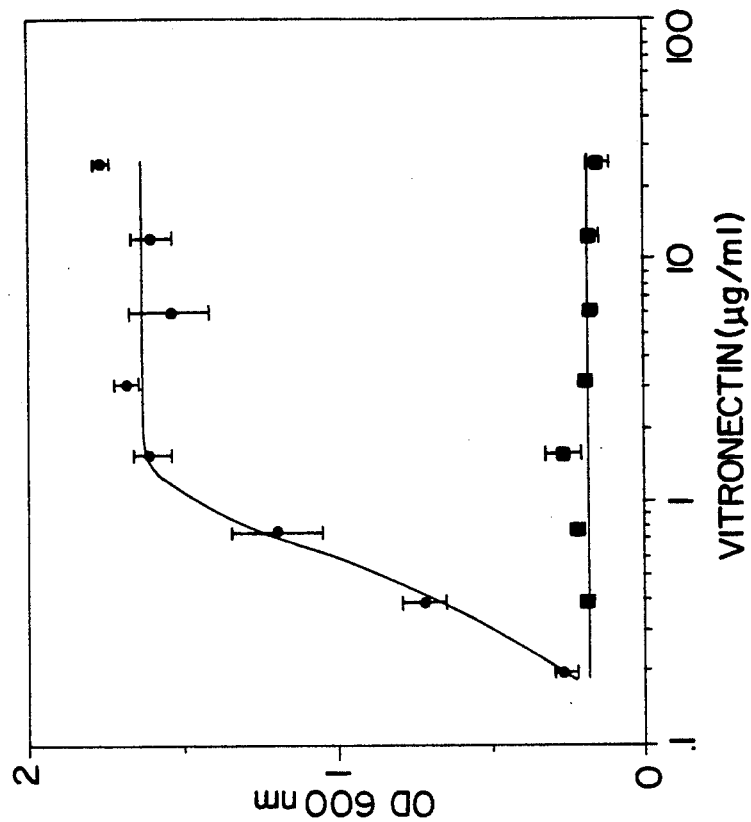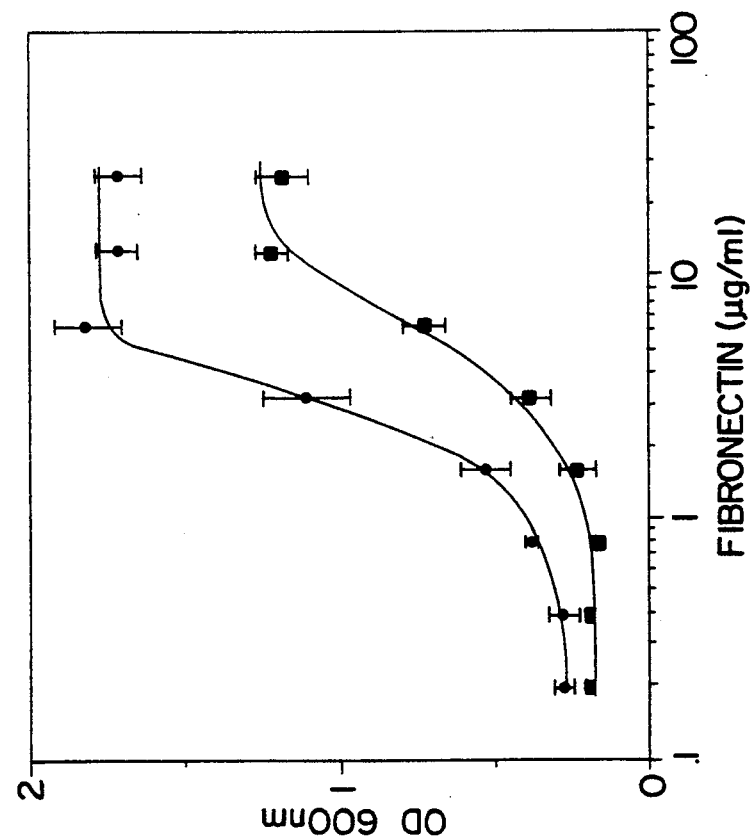

FIBRONECTIN RECEPTOR

BACKGROUND OF THE INVENTION

This invention relates to receptors for adhesion peptides, and more specifically to a novel receptor having affinity for fibronectin.

Multicellular organisms, such as man, have some $10^{14}$ cells which can be divided into a minimum of fifty different types, such as blood cells and nerve cells. During the course of growth and development, cells adhere to other cells, or to extracellular materials, in specific and orderly ways. Such cell adhesion mechanisms appear to be of importance in mediating patterns of cellular growth, migration and differentiation, whereby cells develop specialized characteristics so as to function as, for example, muscle cells or liver cells. Cell adhesion mechanisms are also implicated in dedifferentiation and invasion, notably where cells lose their specialized forms and become metastasizing cancer cells.

The mechanisms underlying the interactions of cells with one another and with extracellular matrices are not fully understood, but it is thought that they are mediated by cell surface receptors which specifically recognize and bind to a cognate ligand on the surface of cells or in the extracellular matrix.

The adhesion of cells to extracellular matrices and their migration on the matrices is mediated in many cases by the binding of a cell surface receptor to an Arg-Gly-Asp containing sequence in the matrix protein (as reviewed in Ruoslahti and Pierschbacher, Science 238:491(1987)). The Arg-Gly-Asp sequence is a cell attachment site at least in fibronectin, vitronectin, various collagens, laminin and tenascin. Despite the similarity of their cell attachment sites, these proteins can be recognized individually by the specific receptors.

Integrins are a family of adhesion receptors which bind to Arg-Gly-Asp binding sites of extracellular matrix membrane proteins via the Arg-Gly-Asp binding sites. They are heterodimeric molecules composed of one alpha ($\alpha$) and one beta ($\beta$) subunit. Several subunits of each kind are known, and various $\alpha\beta$ combinations make up receptors with different ligand specificities.

Eleven distinct alpha chains have thus far been described. Formerly, they have been divided into three main subfamilies based on the beta subunit with which they associate. The $\beta_1$ subfamily includes receptors for fibronectin, various collagens, laminin and tenascin. The $\beta_2$ subfamily consists of leukocyte specific receptors, while the $\beta_3$ subfamily contains multispecific receptors commonly referred to as the platelet glycoprotein IIb-IIIa and the vitronectin receptor. Among the combinations known to exist, the $\alpha_V$ subunit associates with the $\beta_3$ subunit to form a vitronectin receptor and with two recently described $\beta$ subunits called $\beta_X$ and $\beta_S$. The $\alpha_V\beta_X$ integrin is a vitronectin and fibronectin receptor while the ligand specificity of $\alpha_V\beta_S$ is not known.

Because of the importance of integrins in mediating critical aspects of both normal and abnormal cell processes, there exists the need to identify and characterize different integrins. The present invention satisfies this need and provides related advantages as well.

SUMMARY OF THE INVENTION

The present invention provides a substantially pure integrin-type receptor characterized in that it consists of an $\alpha_V$ and a $\beta_1$ subunit. The $\alpha_V\beta_1$ integrin binds to fibronectin and GRGDSPK but does not bind to vitronectin. The $\alpha_V\beta_1$ integrin can be used to determine the presence of a $\alpha_V\beta_1$ ligand and to develop adhesion peptides specific for the various integrins. The presence of the $\alpha_V\beta_1$ can be used to assess ability of cells to adhere to fibronectin.

BRIEF DESCRIPTION OF THE DRAWINGS

FIG. 2 shows the results of cell adhesion assays on fibronectin and vitronectin. The error bars indicate the standard error of the mean of three independent assays.

DETAILED DESCRIPTION OF THE INVENTION

Figure 1:
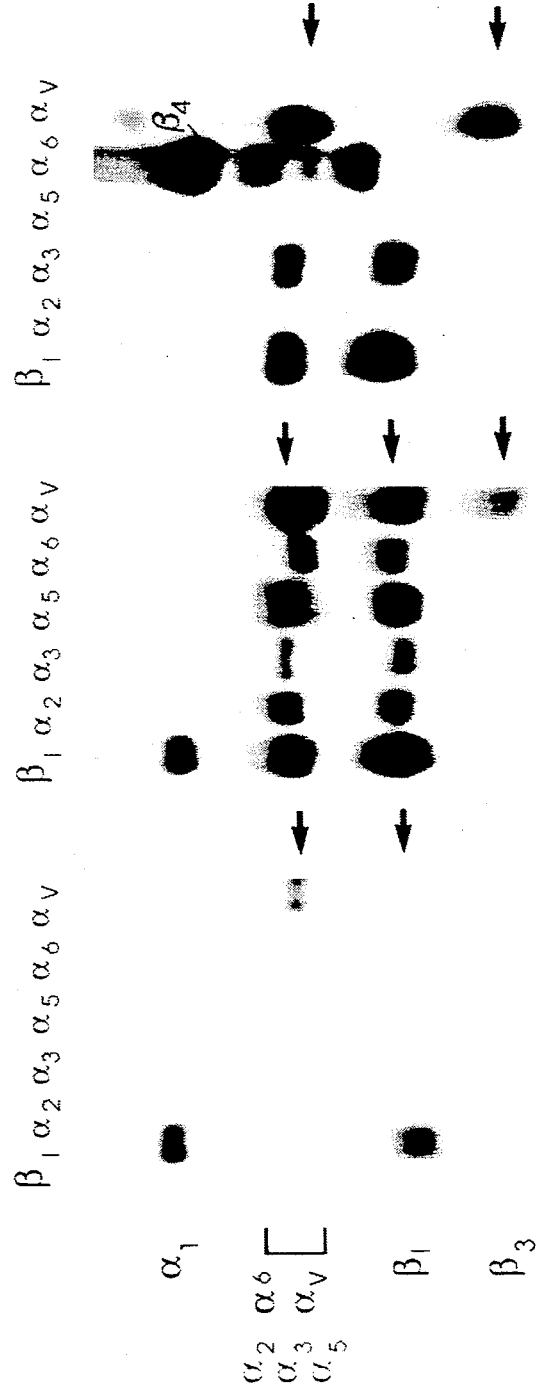
FIG. 1 is a photograph of a gel showing integrin subunits expressed on various cell types.

The invention relates to a new receptor composed of an $\alpha_V$ and a $\beta_1$ subunit, or their immunological equivalents. This integrin-type receptor is herein termed "$\alpha_V\beta_1$ receptor" or "$\alpha_V\beta_1$ integrin." The $\alpha_V\beta_1$ receptor is immunoprecipitated with a monoclonal antibody to the $\alpha_V$ subunit and includes a band in the expected position of the $\beta_1$ subunit, as shown in FIG. 1, left panel.

To confirm the association between the $\alpha_V$ and $\beta_1$ subunits implied by the immunoprecipitation results described above, monoclonal antibodies to each of the subunits were used to isolate receptor complexes from the fibroblast cell line WI-38. A series of antibodies were then used to identify the co-isolated subunit. The material purified by the anti-$\alpha_V$ monoclonal antibody was precipitated by two different anti-$\beta_1$ monoclonal antibodies and by a polyclonal serum to a peptide representing the $\beta_1$ cytoplasmic domain. All three anti-$\beta_1$ reagents recognized the $\alpha_V$-containing integrin. Conversely, the material obtained with a $\beta_1$ monoclonal antibody was immunoprecipitated by two different anti-$\alpha_V$ monoclonal antibodies and by a polyclonal serum to a peptide representing the $\alpha_V$ cytoplasmic domain. These data indicate that the $\alpha_V$ and $\beta_1$ subunits do associate to form a complex.

To investigate the ligand binding specificity of the new $\alpha_V\beta_1$ integrin, affinity chromatography experiments and cell adhesion assays were performed. In the chromatography experiments, detergent extracts of IMR 32 neuroblastoma cells surface labelled with $^{125}I$ were fractionated on fibronectin and GRGDSPK peptide affinity columns. The $\alpha_V\beta_1$ integrin bound to a 110 Kd fragment of fibronectin that contains the cell attachment site. It was eluted from the column with a peptide (GRGDSP), that represents the cell attachment site, but not a related peptide, GRGESP. No additional bands appeared with subsequent EDTA elution. The receptor also bound to a column containing the peptide GRGDSPK coupled to Sepharose and was eluted with the GRGDSP peptide but not with the GRGESP peptide.

Amino acids are identified herein by the standard one-letter abbreviations, as follows:

| Amino Acid | Symbol |
| --- | --- |
| Alanine | A |
| Aspartic acid | D |
| Cysteine | C |
| Glutamine | Q |
| Glutamic acid | E |
| Glycine | G |
| Histidine | H |
| Isoleucine | I |

| Amino Acid | Symbol |
|---|---|
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

To confirm that the eluted material was the $\alpha_V\beta_1$ complex, the peak fractions from each column were pooled and immunoprecipitated with monoclonal antibodies to the $\alpha_V$ and $\beta_1$ subunits. Both antibodies precipitated the same two bands from each column, indicating that the material specifically eluted from each column was, in fact, $\alpha_V\beta_1$.

Cell attachment assays showed that the IMR 32 cells attached to fibronectin but not to vitronectin (FIG. 2) or fibrinogen (not shown). The adhesion of these cells to fibronectin appears to be mediated by the $\alpha_V\beta_1$ complex since the only other integrin detected, $\alpha_1\beta_1$, did not bind fibronectin in the affinity chromatography experiments (see FIG. 1). These cells also attached to collagens I and IV and laminin presumably due to the presence of the $\alpha_1\beta_1$ complex.

The data indicate that the $\alpha_V\beta_1$ integrin subunits associate to form a functional fibronectin receptor. Although molecular heterogeneity due to modifications such as alternative splicing cannot be entirely ruled out, the subunits of the new receptor were immunologically indistinguishable from $\alpha_V$ and $\beta_1$ with at least three antibodies to each subunit. Therefore, by the criteria of electrophoretic mobility and immunological reactivity, the new receptor is composed of $\alpha_V$ and $\beta_1$ subunits or their immunological equivalents.

The new $\alpha_V\beta_1$ does not bind to vitronectin but can be isolated on a GRGDSPK column. This ligand binding pattern appears to be different from that of any of the previously characterized integrins. The ability of this receptor to bind to a GRGDSPK column is a property shared by two vitronectin-binding integrins, $\alpha_V\beta_3$ (Pytela, et al., Proc. Natl. Acad. Sci. USA 82:5766 (1985)), and the platelet receptor $\alpha_{IIB}\beta_3$ (Pytela, et al., Science 231:1559 (1986) (and references therein), which are incorporated herein by reference). A complex between $\alpha_V$ and the recently described $\beta_S$ subunit may also belong to this group (Freed, et al., EMBO 8:2955 (1989), which is incorporated herein by reference). Another recently described complex of $\alpha_V(\alpha_V\beta_X)$ binds to both fibronectin and vitronectin (Cheresh et al., Cell 57:59 (1989), which is incorporated herein by reference).

Fibronectin-binding integrins of the $\beta_1$ class ($\alpha_5\beta_1$) do not bind to vitronectin and unlike the $\alpha_V\beta_1$ integrin described here, do not bind detectably to the GRGDSPK column. Therefore, the $\alpha_V\beta_1$ complex appears to have a distinct intermediate specificity between the vitronectin binding integrins and the $\beta_1$ class integrins.

Three different $\alpha$ subunits have been shown to associate with more than one $\beta$ subunit. Two of these, $\alpha_4$ and $\alpha_6$, can pair with either one of two $\beta$ subunits. The $\alpha_V$ subunit appears to be especially versatile since it has already been shown to be capable of associating with four $\beta$ subunits. Moreover, the association between $\alpha_V$ and $\beta_1$ described here unexpectedly crosses the boundaries of two previously proposed integrin classes, forcing a reevaluation of the currently accepted integrin classification.

Since receptors for collagens, laminin and fibronectin all share a common $\beta$ subunit, it has been proposed that the $\alpha$ subunit determines the specificity of integrins. The new $\alpha_V\beta_1$ integrin described here is a fibronectin receptor, whereas $\alpha_V\beta_3$ is a vitronectin receptor. This result, along with the demonstration that $\alpha_V\beta_X$ binds to fibronectin, shows that the $\beta$ subunit plays a greater role in determining receptor specificity than thought previously.

The $\alpha_V\beta_1$ is useful in assaying the ability of cells to attach to extracellular matrices; the presence of $\alpha_V\beta_1$ on the cell surface indicates the ability to attach to fibronectin. The presence of the $\alpha_V\beta_1$ integrin is detected in an immunoassay format using an antibody against each of the subunits as described in Example I or by a modification of that immunoassay format. Such assays are well known to those skilled in the art. See generally, ANTIBODIES; A LABORATORY MANUAL (Harlow and Lane, eds.) Cold Spring Harbor Laboratory (1988), which is incorporated herein by reference.

Another area where the $\alpha_V\beta_1$ receptor is useful is the analysis of ligands for integrins. The specificity of such ligands is important. For example, synthetic peptides containing the RGD sequence that bind to the platelet integrin gp IIb/IIIa but not to other integrins are being developed into anti-platelet pharmaceuticals.

The ability of a compound to interact with the $\alpha_V\beta_1$ integrin can be assessed by affinity chromatography as described under Example II. A cell attachment assay can be used as described under Example III when the contribution by other integrins possessed by the test cells can be excluded. Finally an enzyme immunoassay format or a radioreceptor assay can be used as described in Hautanen et al., J. Biol. Chem. 264:1347–1442 (1989); Gehlsen et al., J. Biol. Chem., in press (1989).

The following examples are intended to illustrate but not limit the invention.

EXAMPLE I

Identification of $\alpha_V\beta_1$ Integrin

Antibodies to the integrin subunits were prepared as indicated in the following table:

TABLE I

| subunit | host | monoclonal or polyclonal | immunogen | reference or confirmation |
|---|---|---|---|---|
| $\alpha_V$ | mouse | monoclonal Mab 147 | purified vitronectin receptor | immunoblotting; reactive with $\alpha_V$ subunit |
| $\alpha_V$ | mouse | Mab 59 | purified vitronectin receptor | immunoblotting; reactive with $\alpha_V$ subunit |
| $\alpha_V$ | rabbit | polyclonal | KRVRPPQEE-QEREQLQPH-ENGEGNSET | Freed et al. EMBO J. 8:2955 (1989) |
| $\alpha_5$ | rabbit | polyclonal | EKAQLKP-PATSDA | immunoblotting; reactive with $\alpha_5$ subunit |
| $\alpha_6$ | mouse | monoclonal GoH3 | $\alpha_6$ | Sonneberg et al., J. Biol. Chem. 263:14030 (1988) |
| $\alpha_2$ | mouse | monoclonal PIH5 | $\alpha_2$ | Wagner and Carter J. Cell Biol. 105:1073 (1987) |
| $\alpha_3$ | rabbit | polyclonal | cytoplasmic | Hynes et al., |

TABLE I-continued

| sub-unit | host | monoclonal or polyclonal | immunogen | reference or confirmation |
|---|---|---|---|---|
| $\beta_1$ | rabbit | polyclonal | domain of $\alpha_3$ subunit KKKEKEKMN-AKWDTGENP-IYSAVTTVV-NPKYEGK | J. Cell Biol. 109:409 (1989) immunoblotting; reactive with $\beta_1$ subunit |
| $\beta_1$ | mouse | monoclonal LM 534 LM 442 | purified fibronectin receptor | immunoblotting; reactive with $\beta_1$ subunit |

Human neuroblastoma cells (IMR 32; ATCC Accession No. CCL 127), lung cell fibroblasts (WI-38; ATCC Accession No. CCL 75), for example, (WI-38; ATCC Accession No. CCL 757) and glioblastoma cells (U251) were surface labeled with $^{125}I$ and lactoperoxidase according to the method of Pytela et al., Cell 40:191-198 (1985), which is incorporated herein by reference, and extracted with a buffer containing a 0.5% Triton-X-100, 150 mM NaCl, 1 μg/ml leupeptin, 1 mg/ml aprotinin, 0.4 μg/ml pepstatin and 10 mM Tris, pH 7.2. Integrin heterodimers were immunoprecipitated with antibodies specific for either the $\beta_1$ or $\alpha$ subunits and analyzed by SDS-PAGE. Briefly, the extracts were clarified at 15,000 rpm and precleared by an incubation with preimmune rabbit or mouse IgG-Sepharose. Following an incubation with the primary antibodies, immunocomplexes were uncovered with either Sepharose-Protein A or Sepharose-goat anti-mouse IgG.

$\alpha_V$-containing integrins and $\beta_1$-containing integrins were immunopurified from the WI-38 extract on anti-$\alpha_V$ (Mab 147) and anti-$\beta_1$ (Mab LM 534) Sepharose columns respectively. The column was eluted with 50 mM glycine-HCl pH 3, containing 0.5% Triton-X-100. After neutralization, the material was divided in three aliquots for immunoprecipitation with anti-$\beta_1$ antibodies or anti-$\alpha_V$ antibodies and the immunoprecipitates were analyzed by SDS-PAGE substantially as described above. In each case association between the $\alpha_V$ and the $\beta_1$ subunits was found.

EXAMPLE II

Analysis of Ligand Specificity and Purification of $\alpha_V\beta_1$ Integrins

IMR 32 cells were surface labeled with $^{125}I$ and lysed in 200 mM octylglucoside, 150 mM NaCl, 1 mM CaCl$_2$, 1 mM MgCl$_2$, 1 mM MnCl$_2$, 1 μg/ml leupeptin, 1 μg/ml aprotinin, 0.4 μg/ml pepstatin, and 10 mM Tris, pH 7.2. The cell extract was applied to a 110 kD fibronectin fragment-Sepharose column and the column was washed with 50 mM octylglucoside, 1 mM CaCl$_2$, 1 mM MgCl$_2$, 1 mM MnCl$_2$, 150 mM NaCl, and 10 mM Tris, pH 7.2, alone and with 1 mg/ml GRGESP peptide. The column was subsequently eluted with 1 mg/ml GRGDSP peptide followed by elution with 10 mM EDTA. IMR 32 cell extract was also fractionated by identical means on a GRGDSPK column.

These procedures were similar to those described in Pytela et al., Meth. Enzymol. 144:475-489 (1987); and Gailit and Ruoslahti, J. Biol. Chem. 263:12927-12932 (1988), which are incorporated herein by reference. The eluates from each of these columns contained an integrin with an $\alpha$ and a $\beta$ subunit. The peak fractions were pooled and immunoprecipitated with the anti-$\alpha_V$ (Mab 147), or anti-$\beta_1$ (Mab LM 534) described in Example I. The integrin bound to the column was found to precipitate with both anti-$\alpha_V$ and anti-$\beta_1$, indicating that it is an association of the $\alpha_V$ and $\beta_1$ subunits.

EXAMPLE III

Cell Adhesion Assays

Microtiter plates were coated with various concentrations of fibronectin and vitronectin and postcoated with 0.05% bovine serum albumin. After washing, approximately $10^5$ IMR 32 (human neuroblastoma; ATCC CCl 127) or MG-63 (human osteosarcoma; ATCC CCL 1427) cells were plated per well and incubated at 37° C. for 90 minutes. The attached cells were fixed in 3% paraformaldehyde and stained with 0.5% crystal violet. The attachment was quantitated by reading the absorbance at 600 nm. As shown in FIG. 2, the IMR 32 cells attach to fibronectin, but not to vitronectin or fibrinogen, whereas the MG-63 cells attach to all three substrates.

Although the invention has been described with reference to the presently-preferred embodiment, it should be understood that various modifications can be made without departing from the spirit of the invention. Accordingly, the invention is limited only by the following claims.

We claim:

1. A substantially pure active integrin comprising subunits $\alpha_V$ and $\beta_1$ or their immunological equivalents, wherein said integrin binds to GRGDSPK in a cell adhesion assay.

* * * * *

UNITED STATES PATENT AND TRADEMARK OFFICE
CERTIFICATE OF CORRECTION

PATENT NO. : 5,169,930
DATED : December 8, 1992
INVENTOR(S) : Erkki I. Ruoslahti et al It is certified that error appears in the above-indentified patent and that said Letters Patent is hereby corrected as shown below:

Column 1, line 5, insert the following:

--This invention was made with government support under Grant number CA 42507, awarded by the National Institutes of Health and under the Cancer Center Support Grant number CA 30199. The government has certain rights in the invention.--.

Column 2, line 42, please delte the space between $\alpha_v$ and $\beta_1$ to read: $\alpha_v\beta_1$.

Column 6, line 29, please delete "CC1" and insert therefore --CCL--.

Signed and Sealed this

Twenty-first Day of February, 1995

Attest:

BRUCE LEHMAN

Attesting Officer       Commissioner of Patents and Trademarks